United States Patent
Kamei et al.

(10) Patent No.: US 10,241,001 B2
(45) Date of Patent: Mar. 26, 2019

(54) ANTIFOG PROPERTY EVALUATING APPARATUS AND ANTIFOG PROPERTY EVALUATING METHOD

(71) Applicant: KYOWA INTERFACE SCIENCE CO., LTD., Niiza, Saitama (JP)

(72) Inventors: Shinichi Kamei, Niiza (JP); Makoto Uchiumi, Niiza (JP); Yuichiro Higo, Niiza (JP)

(73) Assignee: KYOWA INTERFACE SCIENCE CO., LTD., Niiza, Saitama (JP)

( * ) Notice: Subject to any disclaimer, the term of this patent is extended or adjusted under 35 U.S.C. 154(b) by 103 days.

(21) Appl. No.: 15/341,150

(22) Filed: Nov. 2, 2016

(65) Prior Publication Data

US 2017/0122836 A1    May 4, 2017

(30) Foreign Application Priority Data

Nov. 4, 2015 (JP) ................ 2015-216697

(51) Int. Cl.
| | |
|---|---|
| *G01M 11/02* | (2006.01) |
| *G01N 25/66* | (2006.01) |
| *G02B 1/18* | (2015.01) |
| *G02B 7/02* | (2006.01) |
| *G06T 7/00* | (2017.01) |
| *G02B 27/00* | (2006.01) |

(52) U.S. Cl.
CPC ......... *G01M 11/0285* (2013.01); *G01N 25/66* (2013.01); *G02B 1/18* (2015.01); *G02B 7/023* (2013.01); *G06T 7/0028* (2013.01); *G02B 27/0006* (2013.01); *G06T 2207/10004* (2013.01)

(58) Field of Classification Search
CPC ...... G01M 11/0285; G01N 25/66; G02B 1/18
USPC ......................................... 348/135
See application file for complete search history.

(56) References Cited

U.S. PATENT DOCUMENTS 5,355,252 A    10/1994    Haraguchi

FOREIGN PATENT DOCUMENTS

| DE | 40 28 084 A1 | 3/1992 |
|---|---|---|
| FR | 2 974 904 A1 | 11/2012 |
| JP | 5-203878 A | 8/1993 |
| JP | 2003-050219 A | 2/2003 |
| JP | 3564085 B2 | 2/2003 |
| JP | 2003050219 A  * | 2/2003 |

(Continued)

OTHER PUBLICATIONS

Office Action of Japanese Patent Office issued in Application No. 2015-216697 dated Sep. 27, 2016 (3 pages).

(Continued)

*Primary Examiner* — Jeffery A Williams
(74) *Attorney, Agent, or Firm* — Flynn Thiel, P.C.

(57) ABSTRACT

There are provided an antifog property evaluating apparatus and an antifog property evaluating method capable of quantitatively and objectively evaluating an antifog property in a more realistic situation. The antifog property evaluating apparatus includes: fogging generation devices configured to generate the fogging of a surface of a sample; an object disposed at a position different from that of the sample; an imaging device configured to image the object via the sample; and an evaluation device configured to evaluate the antifog property of the sample on the basis of object images acquired by imaging the object.

13 Claims, 9 Drawing Sheets

(56) References Cited

FOREIGN PATENT DOCUMENTS

| | | |
|---|---|---|
| JP | 2007-024873 A | 2/2007 |
| JP | 2010-190601 A | 9/2010 |
| JP | 5015183 B2 | 9/2010 |

OTHER PUBLICATIONS

Office Action of German Patent Office issued in German Application No. 10 2016 120 992.9 dated Nov. 21, 2018 (5 pages).

* cited by examiner

ANTIFOG PROPERTY EVALUATING APPARATUS AND ANTIFOG PROPERTY EVALUATING METHOD

BACKGROUND OF THE INVENTION

1. Field of the Invention

The present invention relates to an apparatus and a method for evaluating antifog properties of window glasses, mirrors, or various lenses, for example.

2. Description of the Related Art

Evaluation on the antifog properties, which indicate tolerance to fogging, of window glasses, mirrors, or various lenses, for example, has been conducted in conventional techniques mainly by sensory tests by means of visual observation. Examples of such a sensory test include a breath antifog property test, a steam antifog property test, and a low-temperature antifog property test. In the breath antifog property test, a sample is breathed on to visually check the state of fogging in the sample. The antifog property of the sample is evaluated on a scale of about three to four levels on the basis of the presence or absence of fogging, the degree of blur in sight seen via transmission through the sample or reflection by the sample, etc. In the steam antifog property test, a sample is placed above hot water in a thermostatic bath to visually check the deposition state of water droplets on the sample. The antifog property of the sample is evaluated on a scale of about three to four levels on the basis of the presence or absence of the water droplets, the size of the water droplets, etc. In the low-temperature antifog property test, the presence or absence of fogging is evaluated on a scale of two levels when a sample cooled in a refrigerator or a freezer (for example, −20 to 5° C.) is brought back to a normal environment (for example, 20° C. and 65% RH). In these conventional sensory tests, however, evaluation greatly varies from person to person, and thus lacks in stability. Therefore, it has been difficult to evaluate the antifog property quantitatively and objectively.

In view of this, a method for objectively evaluating an antifog property by projecting an image of an object drawing a plurality of vertical lines or a grid on a sample in the above low-temperature antifog property test and measuring a condensation area (fogging area) on a surface of the sample on the basis of such vertical lines or grid, for example, has been proposed (see Patent Literature 1, for example). Also, a method for calculating an antifog property evaluation index on the basis of the degree of scattering of spot light projected on a sample to quantitatively and objectively evaluate the antifog property of the sample on the basis of the antifog property evaluation index has been proposed by the present applicants (see Patent Literature 2, for example).

Patent Literature 1: Japanese Patent No. 3564085
Patent Literature 2: Japanese Patent No. 5015183

SUMMARY OF THE INVENTION

In the evaluating method described in Patent Literature 1 above, however, the size of the condensation area can be evaluated quantitatively, but the degree of fogging, i.e., how much the generation of fogging has lowered the clearness (visibility) of sight seen through, for example, glass (via transmission or reflection) cannot be evaluated quantitatively and objectively. Therefore, in this method, sensory evaluation still needs to be conducted on the degree of fogging.

In the evaluating method described in Patent Literature 2 above, on the other hand, the antifog property evaluation index is calculated on the basis of the degree of scattering of spot light, thus allowing for the quantitative and objective evaluation of the antifog property taking the degree of fogging into account. In this method, however, since the antifog property is evaluated on the basis of the simplified phenomenon, the scattering of the spot light, it is difficult to have a mental image of the actual situation such as how a sight is seen through a car window or how a person's face shown on a bathroom mirror is seen, for example, from the evaluation result. Thus, there is a need for an evaluating method capable of quantitatively and objectively evaluating the antifog property in a more realistic situation.

The present invention has been made in view of the aforementioned problems. It is an object of the invention to provide an antifog property evaluating apparatus and an antifog property evaluating method capable of quantitatively and objectively evaluating an antifog property in a more realistic situation.

(1) An aspect of the present invention provides an antifog property evaluating apparatus including: a fogging generation device configured to generate fogging of a surface of a sample; an object disposed at a position different from that of the sample; an imaging device configured to image the object via the sample; and an evaluation device configured to evaluate an antifog property of the sample on the basis of an object image acquired by imaging the object.

(2) The antifog property evaluating apparatus described in (1) above may further include an image-adjusting lens optical system disposed between the sample and the object.

(3) The antifog property evaluating apparatus described in (1) or (2) above may further include a lighting device configured to illuminate the object with light from behind.

(4) The antifog property evaluating apparatus described in any one of (1) to (3) above may further include: a surface imaging lens optical system to be disposed between the sample and the imaging device; and a retracting device configured to retract the surface imaging lens optical system from an optical path.

(5) In the antifog property evaluating apparatus described in any one of (1) to (4) above, the evaluation device may derive an antifog property evaluation index of the sample on the basis of change in the object image when fogging is generated on the surface of the sample by the fogging generation device.

(6) In the antifog property evaluating apparatus described in (5) above, the evaluation device may derive the antifog property evaluation index on the basis of an area of a region where a pixel value is smaller than or equal to, or larger than or equal to, a predetermined threshold in the object image.

(7) In the antifog property evaluating apparatus described in (5) above, the evaluation device may derive the antifog property evaluation index on the basis of a rate of change in pixel values on a route set in the object image.

(8) In the antifog property evaluating apparatus described in (5) above, the evaluation device may derive the antifog property evaluation index on the basis of a difference or a ratio between pixel values at a first comparison point and a second comparison point in the object image.

(9) In the antifog property evaluating apparatus described in (5) above, the evaluation device may derive the antifog property evaluation index on the basis of a distance from a starting point to a goal point at which a pixel value first becomes larger than or equal to a predetermined threshold on a route set in the object image.

(10) In the antifog property evaluating apparatus described in (5) above, the evaluation device may derive the antifog property evaluation index on the basis of a compression ratio when the object image in an uncompressed state is compressed by a predetermined compression method or a file capacity after compression.

(11) In the antifog property evaluating apparatus described in (5) above, the evaluation device may derive the antifog property evaluation index on the basis of a histogram area of pixel values in the object image.

(12) Another aspect of the present invention provides an antifog property evaluating method including: a fogging generation step of generating fogging of a surface of a sample; an imaging step of imaging an object disposed at a position different from that of the sample via the sample; and an evaluation step of evaluating an antifog property of the sample on the basis of an object image acquired by imaging the object.

(13) In the antifog property evaluating method described in (12) above, an antifog property evaluation index of the sample is derived in the evaluation step on the basis of change in the object image when fogging is generated on the surface of the sample in the fogging generation step.

The antifog property evaluating apparatus and the antifog property evaluating method according to the present invention can provide an advantageous effect of an ability to quantitatively and objectively evaluate the antifog property in a more realistic situation.

DETAILED DESCRIPTION OF THE PREFERRED EMBODIMENTS

An embodiment of the present invention will now be described below with reference to the accompanying drawings.

Figure 1:
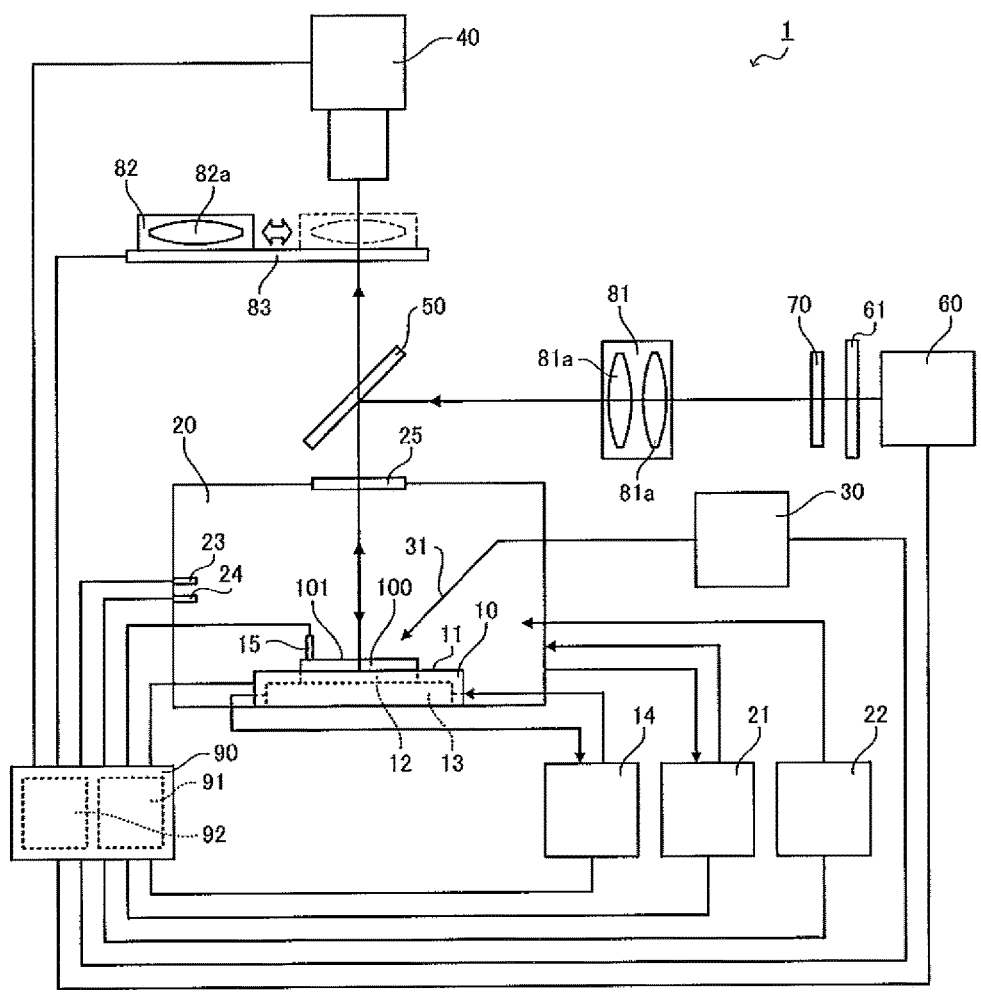
FIG. 1 is a schematic diagram showing an antifog property evaluating apparatus according to an embodiment of the present invention.

An antifog property evaluating apparatus 1 according to an embodiment of the present invention will be described first. FIG. 1 is a schematic diagram showing the antifog property evaluating apparatus 1 according to the present embodiment. As shown in FIG. 1, the antifog property evaluating apparatus 1 includes: a sample stage 10 on which a sample 100 is placed; a measuring chamber 20 configured to house the sample stage 10; a steam spray device 30 connected to the inside of the measuring chamber 20; an imaging device 40 disposed outside the measuring chamber 20; a half mirror 50 disposed between the measuring chamber 20 and the imaging device 40; a lighting device 60 disposed lateral to the half mirror 50; an object 70 disposed between the lighting device 60 and the half mirror 50; an image-adjusting lens optical system 81 disposed between the object 70 and the half mirror 50; a surface imaging lens optical system 82 to be disposed between the half mirror 50 and the imaging device 40; and a control device 90 configured to control the entire antifog property evaluating apparatus 1.

The antifog property evaluating apparatus 1 according to the present embodiment generates the fogging of a surface 101 of the sample 100 by condensation and evaluates the antifog property of the sample 100 on the basis of an image acquired by imaging the object 70 via the fogged sample 100 (i.e., object image). In other words, the anti fog property evaluating apparatus 1 images light from the object 70 after being transmitted through the sample 100 or being reflected at the sample 100, and evaluates the antifog property of the sample 100 on the basis of the resultant image of the object 70.

The sample 100 is a window glass, a lens, or a mirror, for example, for which the antifog property is evaluated. The sample 100 has a plate shape cut out in an appropriate size. To accurately evaluate the antifog property of the sample 100, the thickness of the sample 100 is preferred to be the same as the actual thickness. However, the thickness of the sample 100 is not limited thereto. In evaluating the antifog property of coating applied on a surface of a window glass, for example, an appropriate glass piece having a surface with the coating may be used as the sample 100.

The sample stage 10 is a stand on which the sample 100 to be evaluated for its antifog property is placed. The sample stage 10 includes: a placement surface 11 on which the sample 100 is placed; a Peltier element 12 configured to cool the sample 100; and a heat exchanger 13 configured to cool the heat generation side of the Peltier element 12. A sample stage water circulator 14 configured to circulate cooling water is connected to the heat exchanger 13.

In other words, the sample stage 10 is configured to cool the sample 100 to a temperature lower than or equal to the dew point in the ambient atmosphere and thereby generate condensation on the surface 101 of the sample 100. A surface temperature sensor 15 is disposed on the surface 101 of the sample 100 placed on the sample stage 10. On the basis of the detection result of the surface temperature sensor 15, the control device 90 controls the sample stage 10 to reduce the surface temperature of the sample 100 to a predetermined temperature (for example, 5° C.).

In the present embodiment, the placement surface 11 of the sample stage 10 is formed as a mirror surface. Thus, when the sample 100 is made of a material that transmits light therethrough, such as a window glass or a lens, the object 70 reflected on the placement surface 11 is imaged via the transmission through the sample 100. In this manner, even when the sample 100 transmits light therethrough, the object 70 can be imaged as with the sample 100 that reflects light, such as a mirror. In other words, there is no need to change the arrangement of the imaging device 40, the object 70, etc., depending on whether the sample 100 transmits light therethrough in the present embodiment. Therefore, the entire apparatus can have a simple and compact configuration.

In the present embodiment, the placement surface 11 is formed as a mirror surface by aluminum evaporation. However, a mirror may be disposed between the sample 100 and the sample stage 10 rather than forming the placement surface 11 as a mirror surface. Alternatively, the sample stage 10 may cool the sample 100 by a device other than the Peltier element 12, for example, by direct cooling with the heat exchanger 13.

The measuring chamber 20 is a thermo-hygrostat configured to house the sample 100 together with the sample stage 10 and keep the atmosphere around the sample 100 at a predetermined temperature and a predetermined humidity. The outer wall of the measuring chamber 20 has a jacket structure. A hot and cold water circulator 21 configured to circulate hot water or cold water at a predetermined temperature is connected to the outer wall of the measuring chamber 20. A humidity regulator 22 configured to supply steam to regulate humidity in the measuring chamber 20 is connected to the measuring chamber 20. An in-chamber temperature sensor 23 and an in-chamber humidity sensor 24 are disposed inside the measuring chamber 20. On the basis of the detection results of the in-chamber temperature sensor 23 and the in-chamber humidity sensor 24, the control device 90 controls the hot and cold water circulator 21 and the humidity regulator 22, to keep the atmosphere in the measuring chamber 20 at a predetermined temperature and a predetermined humidity (for example, 20° C. and 50% RH).

An upper part of the measuring chamber 20 includes an observation window 25 made of glass having an appropriate antifog function. The imaging device 40 images the object 70 via the observation window 25. Specifically, light from the object 70 passes through the observation window 25 and travels toward the sample 100, and again passes through the observation window 25 and enters the imaging device 40 after being reflected at the placement surface 11 or the surface 101 of the sample 100.

The antifog method in the observation window 25 is not limited to any particular method. For example, the glass may be heated by a heating wire heater, for example, or an antifog coating, for example, may be applied to a surface of the glass. Alternatively, the measuring chamber 20 may regulate its internal temperature by a device other than the hot and cold water circulator 21.

The steam spray device 30 sprays steam to the surface 101 of the sample 100 in the measuring chamber 20 to forcibly generate the fogging of the surface 101 of the sample 100. In other words, the surface 101 of the sample 100 in the present embodiment can be cooled to a temperature lower than or equal to the dew point to cause condensation naturally. Additionally, water droplets can be applied to the surface 101 of the sample 100 to forcibly generate fogging even when the surface 101 of the sample 100 has a temperature higher than the dew point. A nozzle 31 with its tip being directed toward the surface 101 of the sample 100 is disposed in the measuring chamber 20. The steam spray device 30 sprays steam to the surface 101 of the sample 100 via the nozzle 31.

The imaging device 40 images the object 70 via the sample 100. The imaging device 40 is disposed at a position opposed to the surface 101 of the sample 100 with the observation window 25 and the half mirror 50 being interposed therebetween. As mentioned above, when the sample 100 is a window glass or a lens, the imaging device 40 images the object 70 reflected on the placement surface 11 behind the sample 100 via the transmission through the sample 100. When the sample 100 reflects light, the imaging device 40 images the object 70 reflected on the surface 101 of the sample 100. The imaging device 40 performs imaging in accordance with control made by the control device 90. The imaged image is transmitted to and stored in the control device 90.

The half mirror 50 is disposed between the imaging device 40 and the observation window 25. The half mirror 50 reflects light from the object 70 toward the sample 100 and allows light reflected at the placement surface 11 or the surface 101 of the sample 100 to transmit therethrough to enter the imaging device 40. In the present embodiment, the provision of the half mirror 50 increases flexibility in the arrangement of the imaging device 40, the object 70, and the image-adjusting lens optical system 81, thereby allowing for the compact configuration of the entire apparatus.

The lighting device 60 illuminates the object 70 from behind. The lighting device 60 includes a light source such as a halogen lamp or an LED, for example. The lighting device 60 is disposed so as to project light toward the object 70 from a side opposite to the half mirror 50. Additionally, a diffuser 61 configured to diffuse light is disposed in front of the lighting device 60 (between the lighting device 60 and the object 70).

The object 70 is provided to form an appropriate figure in an image imaged by the imaging device 40. FIGS. 2A to 2D are schematic diagrams showing examples of the object 70. In the present embodiment, while the details thereof will be described later, the antifog property of the sample 100 is evaluated on the basis of change in the object image imaged via the sample 100 due to the fogging of the surface 101 of the sample 100. Thus, the object 70 may be any object capable of having appropriate change in pixel values (such as gray-scale levels, RGB values, or HSV values) in the object image imaged by the imaging device 40.

Figure 2A:
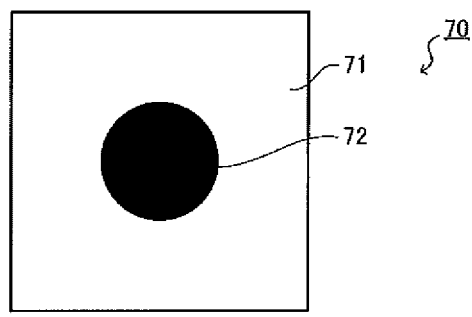
FIGS. 2A to 2D are schematic diagrams showing examples of an object.
Figure 2B:
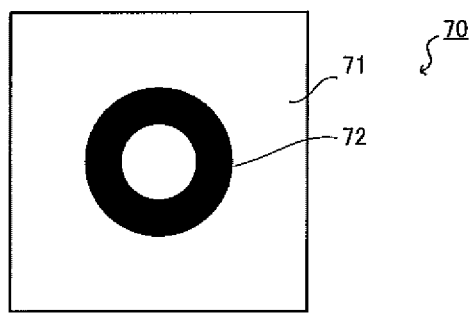

As shown in FIGS. 2A and 2B, examples of the object 70 to be used may include an object in which a metal film 72 that transmits no light is formed on a surface of a transparent substrate 71 made of glass or resin, and an object in which the metal film 72 is interposed between two transparent substrates 71. Since the object 70 is illuminated from behind in the present embodiment, the use of such an object 70 allows for the acquisition of a silhouette image with clear contrast.

In this case, the shape of the metal film 72, i.e., the shape of the figure formed in the image imaged by the imaging device 40 is not limited to any particular shape. The shape may be circular or annular as shown in FIGS. 2A and 2B. Alternatively, the shape may have a polygonal, star, or any other shape including a variety of symbols. Furthermore, a plurality of metal films 72 may be formed on a single substrate 71. In this case, each metal film 72 may have a different shape. Alternatively, an existing droplet standard sample used for the calibration of a contact angle meter may be utilized as the object 70. Such a droplet standard sample allows for highly accurate evaluation of the antifog property due to the high shape accuracy of the metal film 72.

Figure 2C:
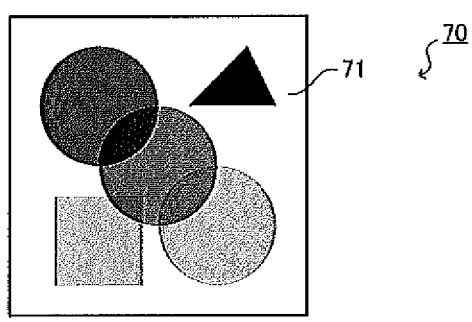
Figure 2D:
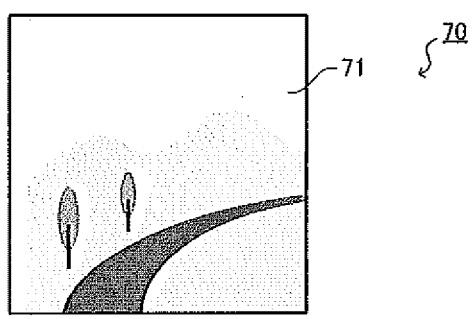

Rather than forming the metal film 72 on the substrate 71, a design, a symbol, a painting, or a picture, for example, may be printed on the substrate 71 as shown in FIGS. 2C and 2D, or an existing positive film, for example, may be used as the object 70. In this case, the use of a gray-scaled picture or a color picture of a landscape or a person, for example, as the object 70 allows the evaluation of the antifog property to be performed under circumstances similar to the actual conditions.

While its diagrammatic illustration will be omitted, a flat plate, a solid, or a statue, for example, made of a material that transmits no light therethrough such as a metal or a resin, for example, may be directly used as the object 70, rather than using the transparent substrate 71.

Referring back to FIG. 1, the image-adjusting lens optical system 81 is configured to adjust the size of the object 70 reflected on the placement surface 11 or the surface 101 of the sample 100 and to adjust the amount of light incident on the imaging device 40. The provision of the image-adjusting lens optical system 81 increases flexibility in the size and arrangement of the object 70, thereby allowing for the compact and efficient configuration of the entire apparatus.

Moreover, since the object 70, together with the image-adjusting lens optical system 81, can be disposed so as to be appropriately spaced apart from the sample 100, the sample 100 and the object 70 can be disposed separately within and outside the measuring chamber 20, respectively. This can prevent the generation of condensation on a surface of the object 70 when generating condensation on the surface 101 of the sample 100. Thus, influence due to the condensation generated on the surface of the object 70 can be eliminated.

Furthermore, the disposition of the image-adjusting lens optical system 81 between the object 70 and the sample 100 concentrates light from the object 70, thereby preventing the image imaged by the imaging device 40 from being excessively darkened by the fogging of the surface 101 of the sample 100. In other words, since there is no need to intensify light for irradiating the object 70, the figure of the object 70 in a more natural state can be reflected on the placement surface 11 or the surface 101 of the sample 100 and can be imaged.

While the image-adjusting lens optical system 81 is constituted by two convex lenses 81a in the present embodiment, the number of the convex lenses 81a that constitute the image-adjusting lens optical system 81 is not limited thereto. Alternatively, the image-adjusting lens optical system 81 may be constituted by a combination of the convex lens 81a and a concave lens. Alternatively, the size of the object 70 reflected on the placement surface 11 or the surface 101 of the sample 100 may be adjusted by providing a zoom mechanism in the image-adjusting lens optical system 81 or by providing a moving mechanism configured to move the image-adjusting lens optical system 81 or the object 70 to change their relative positions.

The surface imaging lens optical system 82 is configured to image the state of condensation on the surface 101 of the sample 100 by the imaging device 40. As mentioned above, the antifog property evaluating apparatus 1 evaluates the antifog property of the sample 100 on the basis of images acquired by imaging the object 70 via the sample 100. Thus, the focal length of the imaging device 40 basically corresponds to the position of the object 70. Accordingly, in the present embodiment, the focal length is changed by inserting the surface imaging lens optical system 82 between the half mirror 50 and the imaging device 40, thereby allowing both of the object 70 and the surface 101 of the sample 100 to be imaged by a single imaging device 40.

The surface imaging lens optical system 82 is configured to include an appropriate convex lens 82a and to be able to be retracted from an optical path by a retracting device 83 controlled by the control device 90. More specifically, in the present embodiment, the surface imaging lens optical system 82 is retracted from the optical path when the object 70 is imaged to evaluate the antifog property. In contrast, the surface imaging lens optical system 82 is disposed on the optical path when the state of condensation on the surface 101 of the sample 100 is observed.

As with the image-adjusting lens optical system 81, the configuration of the surface imaging lens optical system 82 can adopt various known configurations without being limited to any particular configuration. Alternatively, the surface imaging lens optical system 82 may be disposed between the measuring chamber 20 and the half mirror 50 or may be incorporated into the imaging device 40. Alternatively, the retracting device 83 may be configured to move the surface imaging lens optical system 82 by hand.

The control device 90 is configured to control the entire antifog property evaluating apparatus 1 to execute evaluation on the antifog property of the sample 100. The control device 90 is constituted by a computer including storage means such as a hard disk or a flash disk as well as a CPU, a ROM, and a RAM. The control device 90 is electrically connected to the components of the antifog property evaluating apparatus 1. An input device (not shown) such as a keyboard and a mouse and a display device (not shown) such as a liquid crystal display are connected to the control device 90. A user operates the antifog property evaluating apparatus 1 via such devices.

The control device 90 also includes control unit 91 and evaluation unit 92 as functional components implemented by the execution of programs stored, for example, in the hard disk by the CPU. The control unit 91 controls the sample stage 10, the hot and cold water circulator 21, the humidity regulator 22, the steam spray device 30, and the imaging device 40, for example, to generate the fogging of the surface 101 of the sample 100 and executes the imaging of the object 70 via the sample 100. The control unit 91 also controls the retracting device 83 and the imaging device 40 to execute the imaging of the surface 101 of the sample 100. On the basis of the object images acquired by the control unit 91, the evaluation unit 92 derives an antifog property evaluation index for evaluating the antifog property of the sample 100 by a predetermined method. An evaluation device including the evaluation unit 92 may be provided separately from the control device 90.

The arrangement of the components of the above-described antifog property evaluating apparatus 1 is not limited to the one shown in FIG. 1. Different arrangements may be adopted. For example, the sample 100 may be disposed with the surface 101 facing a lateral side, and imaging may be performed by the imaging device 40 disposed on the lateral side. Alternatively, the sample 100 may be disposed with the surface 101 facing downward or in an oblique direction. The surface 101 of the sample 100 facing, for example, the lateral side allows for the evaluation of the antifog property while taking gravitational influence on condensation into account.

A procedure of evaluating an antifog property by the antifog property evaluating apparatus 1 will be described next. In the evaluation of the antifog property, the sample 100 is first placed on the placement surface 11 of the sample stage 10. The sample 100 may be placed by hand or automatically by an appropriate conveyer, for example. Next, the control unit 91 of the control device 90 controls the hot and cold water circulator 21 and the humidity regulator 22 to keep the atmosphere in the measuring chamber 20 at a preset temperature and a preset humidity (atmosphere setting step).

If it is confirmed that the inside of the measuring chamber 20 is being kept at the preset temperature and humidity on the basis of the detection results of the in-chamber temperature sensor 23 and the in-chamber humidity sensor 24, the control unit 91 controls the lighting device 60 and the imaging device 40 to image the object 70 via the sample 100 in order to acquire an object image when no fogging is present on the surface 101 of the sample 100 (imaging step before the generation of fogging). The acquired object image is stored in the storage means included in the control device 90 and displayed on the display device.

Next, the control unit 91 controls the sample stage 10 to cool the sample 100 to a temperature lower than or equal to the dew point in order to generate the fogging of the surface 101 (fogging generation step). At the same time, the control unit 91 also controls the imaging device 40 to image the object 70 via the sample 100 (imaging step after the generation of fogging). In the imaging step after the generation of fogging, the control unit 91 acquires an object image when fogging is present on the surface 101 of the sample 100 at predetermined intervals (for example, every second) in order to record time-varying change of the fogging. The acquired object images are stored in the storage means included in the control device 90 and displayed on the display device.

When fogging is generated on the surface 101 of the sample 100 by the steam spray device 30, the control unit 91 controls the steam spray device 30 to spray steam to the surface of the sample 100 in the fogging generation step. In this case, steam may be sprayed after the surface 101 of the sample 100 is cooled to a predetermined temperature by the sample stage 10.

Once the object images are stored in the storage means, the evaluation unit 92 of the control device 90 next derives the antifog property evaluation index on the basis of the stored object images (evaluation step). The derived antifog property evaluation index is stored in the storage means and displayed on the display device. The evaluation on the antifog property of the sample 100 is completed through the above procedure.

In the imaging step before the generation of fogging and the imaging step after the generation of fogging, the surface 101 of the sample 100 may be imaged together with the imaging of the object 70 via the sample 100. In this case, the control unit 91 controls the retracting device 83 and the imaging device 40 at appropriate timing before and after the imaging of the object 70 to image the surface 101 of the sample 100 to acquire surface images. Intervals to acquire such surface images in the imaging step after the generation of fogging may be the same as, or different from, the intervals to acquire the object images. The observation of the condensation state on the surface 101 along with the evaluation of the antifog property allows for more multilateral evaluation.

Alternatively, only the imaging of the surface 101 of the sample 100 may be performed in the imaging step before the generation of fogging and the imaging step after the generation of fogging by performing the above-described procedure with the surface imaging lens optical system 82 being disposed in advance on the optical path. In this case, change in the state of the surface 101 of the sample 100 can be observed in detail, although the antifog property evaluation index cannot be derived.

Figure 3A:
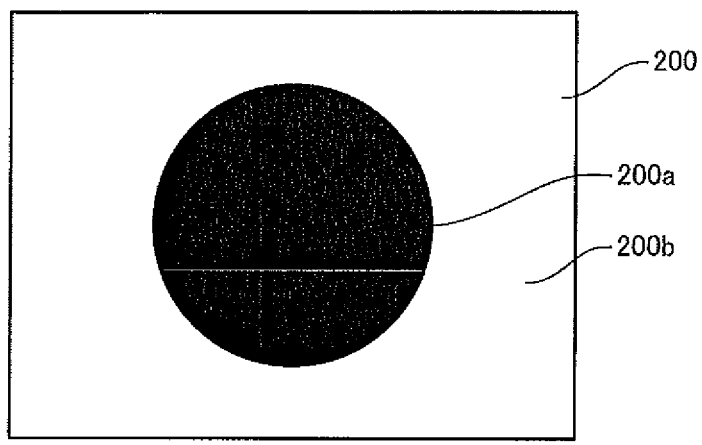
FIG. 3A is a schematic diagram showing one example of an object image acquired when no fogging is present on a surface of a sample.
Figure 3B:
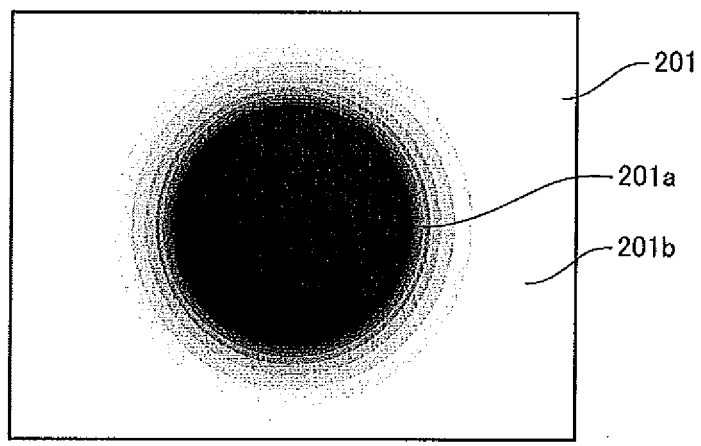
FIG. 3B is a schematic diagram showing one example of an object image acquired when fogging is present on the surface of the sample.

A method for deriving the antifog property evaluation index will be described next in detail. FIG. 3A is a schematic diagram showing one example of an object image 200 acquired when no fogging is present on the surface 101 of the sample 100. FIG. 3B is a schematic diagram showing one example of an object image 201 acquired when fogging is present on the surface 101 of the sample 100. These figures schematically show examples when the object 70 shown in FIG. 2A is imaged.

The image acquired by imaging the object 70 is a silhouette image as mentioned above. Specifically, the metal film 72 of the object 70 transmits no light from the lighting device 60, and thus the metal film 72 is shown as a dark region 200a or 201a that is darker than its surrounding region. The transparent substrate 71 is shown as a light region 200b or 201b that is lighter than the dark region 200a or 201a. When no fogging (condensation) is present on the surface 101 of the sample 100, there is no scattering of light due to fogging. Therefore, even when the object 70 is imaged via the sample 100, the shape of the metal film 72 in the object 70 is clearly shown as illustrated in FIG. 3A, resulting in the object image 200 with a substantially clear boundary (edge) between the dark region 200a and the light region 200b.

When fogging (condensation) is present on the surface 101 of the sample 100, on the other hand, light scatters due to the fogging. Therefore, the shape of the metal film 72 in the object 70 is shown in a blurred manner as illustrated in FIG. 3B, resulting in the object image 201 with an unclear boundary (edge) between the dark region 201a and the light region 201b. Moreover, the light region 201b in the object image 201 has reduced overall brightness as compared to the light region 200b in the object image 200 due to the scattering of light.

In other words, the object image 201 acquired when fogging is present on the surface 101 of the sample 100 is different from the object image 200 acquired when no fogging is present on the surface 101 of the sample 100. More specifically, pixel values (such as gray-scale levels, RGB values, or HSV values) of at least part of pixels in the object image 201 are different from the pixel values of the pixels at the same positions in the object image 200 as a result of the scattering of light due to fogging.

In the present embodiment, the antifog property of the sample 100 can be evaluated quantitatively and objectively by deriving the antifog property evaluation index that quantifies the degree of such change in the object image 201 from the object image 200. Moreover, the degree of change in the object image 201 from the object image 200 represents the degree of change in the visibility of sight via the sample 100 (transmitted or reflected). Thus, the antifog property can be directly evaluated in a more realistic situation.

The method for deriving the antifog property evaluation index can adopt various methods utilizing various known image processing methods and image analysis methods without being limited to any particular method. Note however that the antifog property evaluation index is derived in the present embodiment by any one of six methods to be described below: an area ratio method; a slope ratio method; a contrast ratio method; a distance ratio method; a compression ratio method; and a histogram method. In the following, each of these methods will be described taking, as an example, a case where the object images 200 and 201 shown in FIGS. 3A and 3B are acquired as gray-scaled images with 256 levels of gray.

<Area Ratio Method>

Figure 4A:
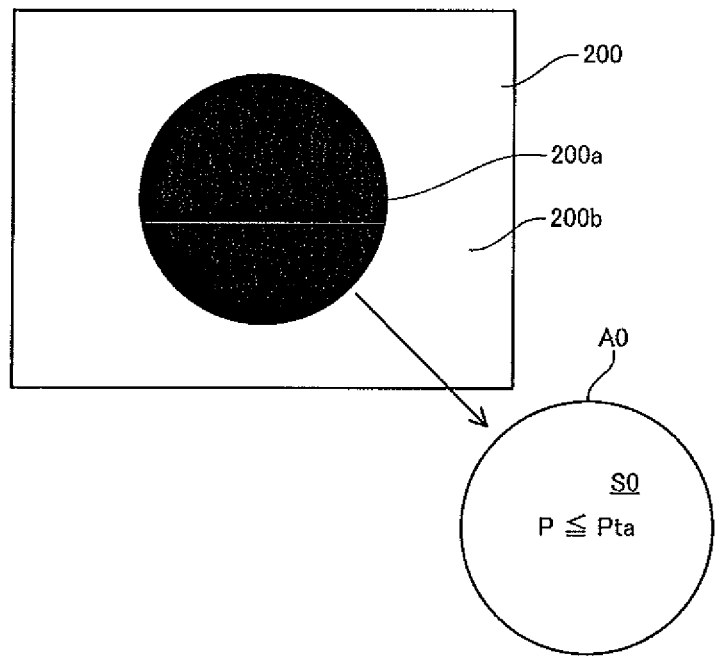
FIGS. 4A and 4B are schematic diagrams showing a general concept of an area ratio method.
Figure 4B:
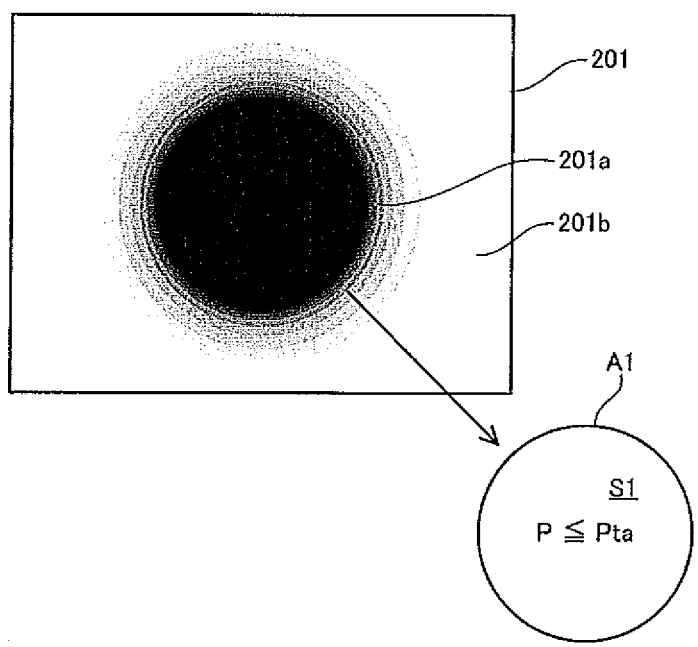

FIGS. 4A and 4B are schematic diagrams showing a general concept of the area ratio method. In the area ratio method, the antifog property evaluation index is derived on the basis of areas S0 and S1 of regions A0 and A1 where pixel values P of pixels in the regions are smaller than or equal to a predetermined threshold Pta in the object images 200 and 201 before and after the generation of fogging. Specifically, the evaluation unit 92 of the control device 90 first derives the area S0 of the region A0 where the pixel values P (here, gray-scale levels) of the pixels in this region are smaller than or equal to the predetermined threshold Pta in the object image 200 acquired when no fogging is present on the sample 100 as shown in FIG. 4A.

Next, the evaluation unit 92 derives the area S1 of the region A1 where the pixel values P of the pixels are smaller than or equal to the predetermined threshold Pta in the object image 201 acquired when fogging is present on the sample 100 as shown in FIG. 4B. The evaluation unit 92 then derives a ratio S1/S0 or S0/S1 between the area S1 and the area S0 as the antifog property evaluation index.

The area S1 becomes smaller than the area S0 as the degree of light scattering due to the fogging of the sample 100 increases, because the dark region 201a is illuminated to brighten it up (i.e., to raise the level of gray). When there is almost no light scattering due to fogging, on the other hand, the area S1 has a value close to the area S0. Therefore, when the ratio S1/S0 is derived as the antifog property evaluation index, the antifog property of the sample 100 becomes higher as the value of the antifog property evaluation index becomes larger (closer to 1), and the antifog property of the sample 100 becomes lower as the value of the antifog property evaluation index becomes smaller. When the ratio S0/S1 is derived as the antifog property evaluation index, the opposite applies.

Note that the value of the area S1 may be directly used as the antifog property evaluation index rather than obtaining the area ratio S1/S0 or S0/S1. When the object images 200 and 201 are acquired as color images, the median value, average value, or weighted average value, for example, of an R (red) value, a G (green) value, and a B (blue) value or an H (hue) value, an S (saturation) value, and a V (value) value may be used as the pixel value P. Alternatively, any one of the R value, the G value, and the B value, or any one of the H value, the S value, and the V value may be used as the pixel value P.

Alternatively, the antifog property evaluation index may be derived on the basis of areas of regions where the pixel values P of their pixels are larger than or equal to the predetermined threshold Pta. In this case, as the degree of light scattering increases, the light region 201b becomes darker. Therefore, the area of the region where the pixel values P of its pixels are larger than or equal to the predetermined threshold Pta becomes smaller accordingly. Alternatively, the object images 200 and 201 may be transformed into binary images on the basis of the predetermined threshold Pta and the obtained images may be displayed on the display device, for example. This can visually show change in the areas of the regions A0 and A1 or change in their shapes.

<Slope Ratio Method>

Figure 5A:
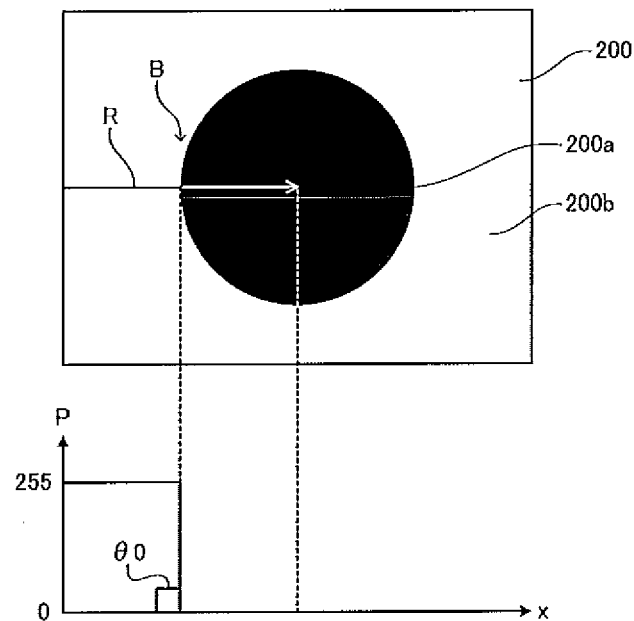
FIGS. 5A and 5B are schematic diagrams showing a general concept of a slope ratio method.
Figure 5B:
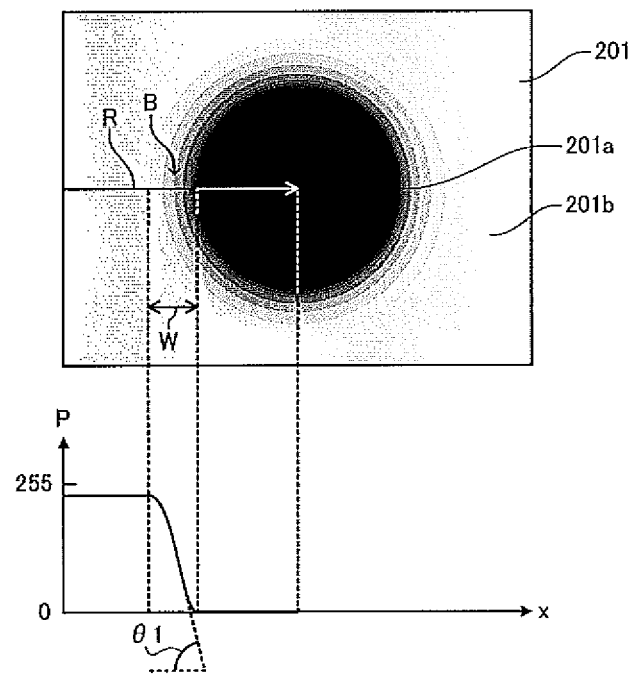

FIGS. 5A and 5B are schematic diagrams showing a general concept of the slope ratio method. In the slope ratio method, the antifog property evaluation index is derived on the basis of a rate of change in the pixel values P of pixels on a route R set in the object images 200 and 201 before and after the generation of fogging. Specifically, the evaluation unit 92 of the control device 90 first sets the route R in a horizontal direction (x direction) extending over the dark region 200a and the light region 200b in the object image 200 acquired when no fogging is present on the sample 100 as shown in FIG. 5A. The evaluation unit 92 then obtains the pixel values P of pixels on the route R to derive an average slope angle $\theta 0$ as a rate of change in the pixel value P at a boundary B.

Next, the evaluation unit 92 sets the same route R as the object image 200 in the object image 201 acquired when fogging is present on the sample 100 as shown in FIG. 5B. The evaluation unit 92 obtains the pixel values P of pixels on the route R to derive an average slope angle $\theta 1$ as a rate of change in the pixel value P in the boundary B. The evaluation unit 92 then derives a ratio $\theta 1/\theta 0$ or $\theta 0/\theta 1$ between the average slope angle $\theta 1$ and the average slope angle $\theta 0$ as the antifog property evaluation index.

In this example, since the object image 200 has high contrast, the pixel value P on the route R in the object image 200 suddenly changes at the boundary B from a substantially constant state at the maximum value (255) to a substantially constant state at an approximately minimum value (0). Thus, the average slope angle $\theta 0$ is approximately 90°. On the route R in the object image 201, on the other hand, as the degree of light scattering due to the fogging of the sample 100 increases, the light region 201b becomes darker and a width W of the boundary B increases. Since the pixel value P gradually changes within such a width W, the average slope angle $\theta 1$ becomes smaller accordingly. When there is almost no light scattering due to fogging, the average slope angle $\theta 1$ has a value close to the average slope angle $\theta 0$.

Therefore, when the ratio $\theta 1/\theta 0$ is derived as the antifog property evaluation index, the antifog property of the sample 100 becomes higher as the value of the antifog property evaluation index becomes larger (closer to 1), and the antifog property of the sample 100 becomes lower as the value of the antifog property evaluation index becomes smaller. When the ratio $\theta 0/\theta 1$ is derived as the antifog property evaluation index, the opposite applies.

As with the case of the area ratio method, the value of the average slope angle $\theta 1$ may be directly used as the antifog property evaluation index. When the object images 200 and 201 are acquired as color images, the median value, average value, or weighted average value, for example, of the R value, the G value, and the B value or the H value, the S value, and the V value may be used as the pixel value P. Alternatively, any one of the R value, the G value, and the B value, or any one of the H value, the S value, and the V value may be used as the pixel value P.

Without being limited to any particular position, the position of the route R can be set anywhere as long as the route R crosses the boundary B where the pixel value P changes. Also, the direction of the route R may be any direction without being limited to the x direction. For the pixel values P to be obtained, only the pixel values P of the pixels on the route R may be obtained, or the average value, for example, of the pixel values P of a pixel on the route R and its adjacent pixel may be obtained. Alternatively, a plurality of routes R may be set, and the antifog property evaluation index may be derived on the basis of the average value of the average slope angles $\theta 0$ in the routes R and the average value of the average slope angles $\theta 1$ in the routes R.

<Contrast Ratio Method>

Figure 6A:
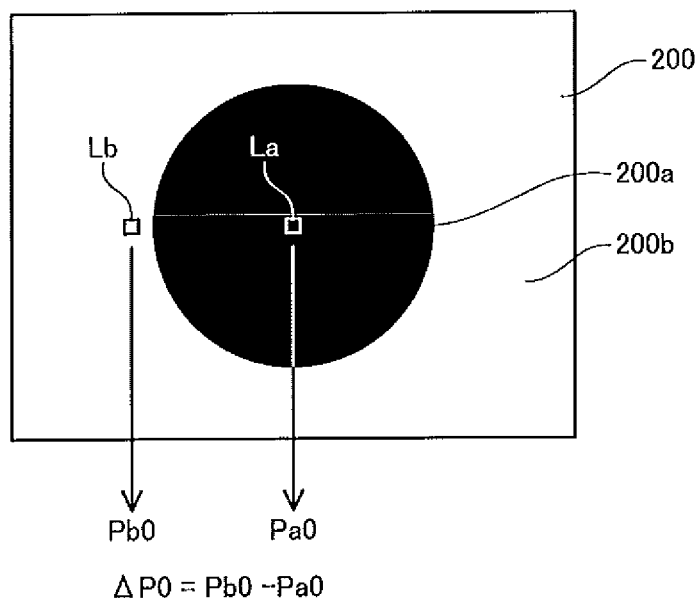
FIGS. 6A and 6B are schematic diagrams showing a general concept of a contrast ratio method.
Figure 6B:
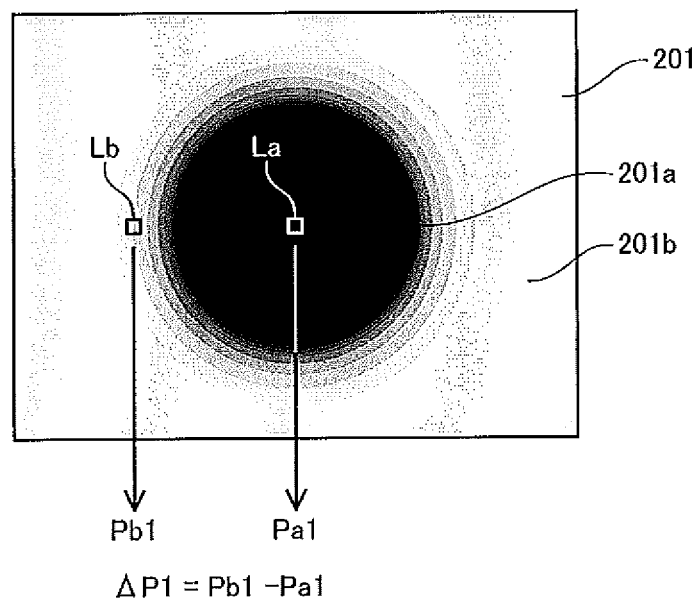

FIGS. 6A and 6B are schematic diagrams showing a general concept of the contrast ratio method. In the contrast ratio method, the antifog property evaluation index is derived on the basis of differences $\Delta P0$ and $\Delta P1$ between pixel values P at a first comparison point La and a second comparison point Lb set in the object images 200 and 201 before and after the generation of fogging. Specifically, the evaluation unit 92 of the control device 90 first sets the first comparison point La in the dark region 200a and sets the second comparison point Lb in the light region 200b in the object image 200 acquired when no fogging is present on the sample 100 as shown in FIG. 6A. Thereafter, the evaluation unit 92 obtains a pixel value Pa0 at the first comparison point La and a pixel value Pb0 at the second comparison point Lb. The evaluation unit 92 then derives the difference $\Delta P0$ (=Pb0−Pa0) therebetween.

Next, in the object image 201 acquired when fogging is present on the sample 100, the evaluation unit 92 sets the first comparison point La and the second comparison point Lb at the same positions as the object image 200 as shown in FIG. 6B. Thereafter, the evaluation unit 92 obtains a pixel value Pa1 at the first comparison point La and a pixel value Pb1 at the second comparison point Lb. The evaluation unit 92 then derives the difference ΔP1 (=Pb1−Pa1) therebetween. The evaluation unit 92 then derives a ratio ΔP1/ΔP0 or ΔP0/ΔP1 between the difference ΔP1 and the difference ΔP0 as the antifog property evaluation index.

In this example, since the object image 200 has high contrast as mentioned above, the pixel value Pa0 at the first comparison point La has an approximately minimum value (0) and the pixel value Pb0 at the second comparison point Lb has an approximately maximum value (255) in the object image 200. Therefore, the difference ΔP0 has an approximately maximum value (255). In the object image 201, on the other hand, as the degree of light scattering due to the fogging of the sample 100 increases, the light region 201b becomes darker and thus the pixel value Pb1 at the second comparison point Lb decreases. In the object image 201, as the degree of light scattering due to the fogging of the sample 100 increases, the dark region 201a becomes lighter and thus the pixel value Pa1 at the first comparison point La increases. Therefore, the difference ΔP1 becomes much smaller accordingly. This fact is very unique discovery. Therefore, the difference ΔP1 becomes smaller accordingly. When there is almost no light scattering due to fogging, the difference ΔP1 has a value close to the difference ΔP0.

Therefore, when the ratio ΔP1/ΔP0 is derived as the antifog property evaluation index, the antifog property of the sample 100 becomes higher as the value of the antifog property evaluation index becomes larger (closer to 1), and the antifog property of the sample 100 becomes lower as the value of the antifog property evaluation index becomes smaller. When the ratio ΔP0/ΔP1 is derived as the antifog property evaluation index, the opposite applies.

As with the cases of the above-described methods, the value of the difference ΔP1 may be directly used as the antifog property evaluation index. When the object images 200 and 201 are acquired as color images, the median value, average value, or weighted average value, for example, of the R value, the G value, and the B value or the H value, the S value, and the V value may be used as the pixel value P. Alternatively, any one of the R value, the G value, and the B value, or any one of the H value, the S value, and the V value may be used as the pixel value P.

Without being limited to any particular positions, the first comparison point La and the second comparison point Lb can be set at appropriate positions in accordance with, for example, the configuration of the object 70. For the pixel values P to be obtained, only the pixel values P of the pixels at the first comparison point La and the second comparison point Lb may be obtained, or the average values, for example, of the pixel values P of the pixels at the first comparison point La and the second comparison point Lb and their adjacent pixels may be obtained. Alternatively, a pixel having the minimum pixel value P may be used as the first comparison point La and a pixel having the maximum pixel value P may be used as the second comparison point Lb in the entire image or on a predetermined route in the image, for example, rather than fixing the positions of the first comparison point La and the second comparison point Lb.

Alternatively, a plurality of first comparison points La and a plurality of second comparison points Lb may beset, and the anti fog property evaluation index may be derived on the basis of the average value of the plurality of differences ΔP0 and the average value of the plurality of differences ΔP1. Alternatively, the antifog property evaluation index may be derived on the basis of not the differences ΔP0 and ΔP1 but a ratio Pb0/Pa0 or Pa0/Pb0 between the pixel value Pa0 and the pixel value Pb0 and a ratio Pb1/Pa1 or Pa1/Pb1 between the pixel value Pa1 and the pixel value Pb1.

<Distance Ratio Method>

Figure 7A:
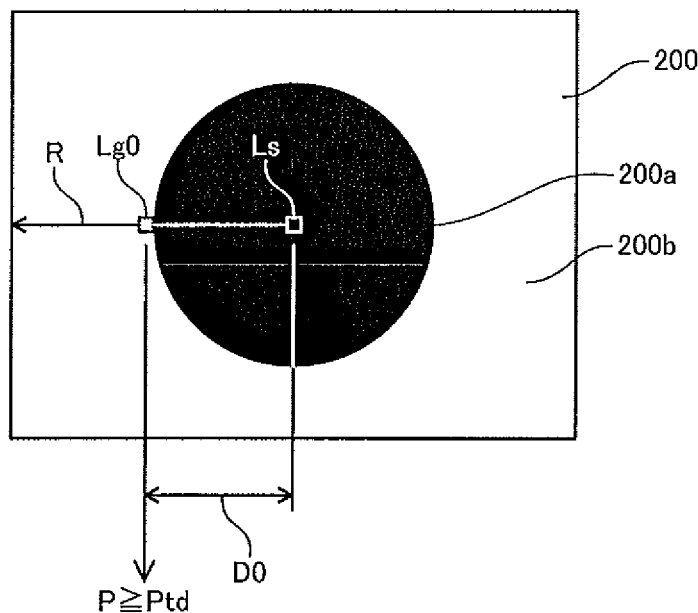
FIGS. 7A and 7B are schematic diagrams showing a general concept of a distance ratio method.
Figure 7B:
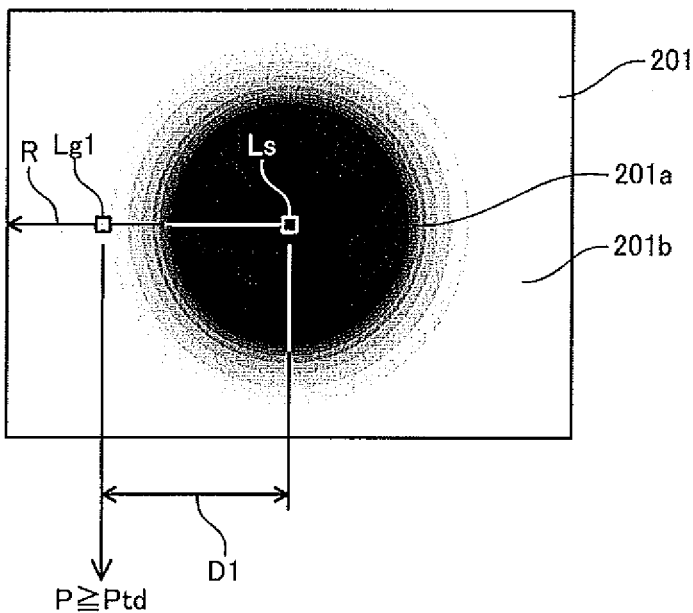

FIGS. 7A and 7B are schematic diagrams showing a general concept of the distance ratio method. In the distance ratio method, the antifog property evaluation index is derived on the basis of distances D0 and D1 from a starting point Ls to goal points Lg0 and Lg1 at which the pixel value P becomes larger than or equal to a predetermined threshold Ptd for the first time on a route R set in the object images 200 and 201 before and after the generation of fogging. Specifically, the evaluation unit 92 of the control device 90 first sets the starting point Ls in the dark region 200a in the object image 200 acquired when no fogging is present on the sample 100 as shown in FIG. 7A. The evaluation unit 92 then sets the route R in a horizontal direction (x direction) from the starting point Ls. Thereafter, the evaluation unit 92 obtains, sequentially from the starting point Ls, the pixel values P of the pixels on the route R. The evaluation unit 92 sets, as the goal point Lg0, a point (pixel) at which the pixel value P becomes larger than or equal to the predetermined threshold Ptd for the first time. Thereafter, the evaluation unit 92 derives the distance D0 from the starting point Ls to the goal point Lg0.

Next, in the object image 201 acquired when fogging is present on the sample 100, the evaluation unit 92 sets the starting point Ls at the same position as the object image 200 and sets the same route R as the object image 200 as shown in FIG. 7B. Thereafter, the evaluation unit 92 obtains, sequentially from the starting point Ls, the pixel values P of the pixels on the route R. The evaluation unit 92 sets, as the goal point Lg1, a point at which the pixel value P becomes larger than or equal to the predetermined threshold Ptd for the first time. The evaluation unit 92 then derives the distance D1 from the starting point Ls to the goal point Lg1. Finally, the evaluation unit 92 derives a ratio D1/D0 or D0/D1 between the distance D0 and the distance D1 as the antifog property evaluation index.

As the degree of light scattering due to the fogging of the sample 100 increases, an area around the dark region 201a becomes darker (i.e., the level of gray is lowered). Therefore, the distance D1 becomes larger than the distance D0 accordingly. When there is almost no light scattering due to fogging, on the other hand, the distance D1 has a value close to the distance D0. Therefore, when the ratio D1/D0 is derived as the antifog property evaluation index, the antifog property of the sample 100 becomes higher as the value of the antifog property evaluation index becomes smaller (closer to 1), and the antifog property of the sample 100 becomes lower as the value of the antifog property evaluation index becomes larger. When the ratio D0/D1 is derived as the antifog property evaluation index, the opposite applies.

As with the cases of the above-described methods, the value of the distance D1 may be directly used as the antifog property evaluation index. When the object images 200 and 201 are acquired as color images, the median value, average value, or weighted average value, for example, of the R value, the G value, and the B value or the H value, the S value, and the V value may be used as the pixel value P. Alternatively, any one of the R value, the G value, and the B value, or any one of the H value, the S value, and the V value may be used as the pixel value P.

Without being limited to any particular position, the starting point Ls can be set at an appropriate position in accordance with, for example, the configuration of the object 70. Also, the direction of the route R may be any direction without being limited to the x direction. For the pixel values P to be obtained, only the pixel values P of the pixels on the route R may be obtained, or the average value, for example, of the pixel values P of a pixel on the route R and its adjacent pixel may be obtained. Alternatively, a plurality of starting points Ls or a plurality of routes R may be set, and the antifog property evaluation index may be derived on the basis of the average value of the plurality of distances D0 and the average value of the plurality of distances D1.

<Compression Ratio Method>

Figure 8A:
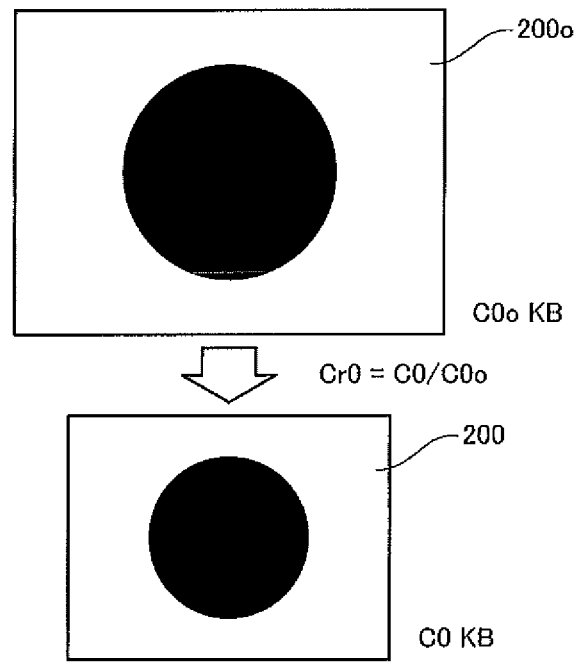
FIGS. 8A and 8B are schematic diagrams showing a general concept of a compression ratio method.
Figure 8B:
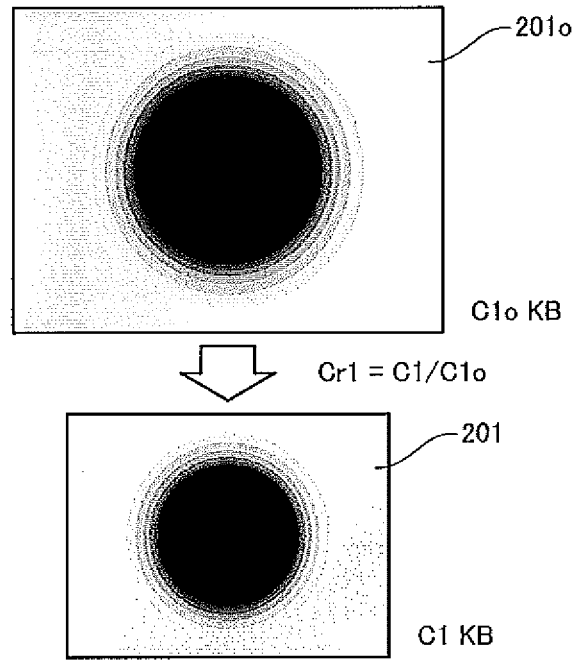

FIGS. 8A and 8B are schematic diagrams showing a general concept of the compression ratio method. In the compression ratio method, the antifog property evaluation index is derived on the basis of compress ion ratios Cr0 and Cr1 when uncompressed object images 200o and 201o before and after the generation of fogging are compressed by a predetermined image compression method. Specifically, the evaluation unit 92 of the control device 90 first compresses the uncompressed (for example, a RAW format or a BMP format) object image 200o acquired when no fogging is present on the sample 100 by the predetermined image compression method to generate the object image 200 in a JPEG format, for example, as shown in FIG. 8A. The evaluation unit 92 then obtains a file capacity C0o of the object image 200o and a file capacity C0 of the object image 200 to derive a compression ratio Cr0 (=C0/C0o).

Next, the evaluation unit 92 compresses the uncompressed object image 201o acquired when fogging is present on the sample 100 by the same image compression method as with the object image 200o to generate the object image 201 in the same format as the object image 200 as shown in FIG. 8B. The evaluation unit 92 then obtains a file capacity C1o of the object image 201o and a file capacity C1 of the object image 201 to derive a compression ratio Cr1 (=C1/C1o). Finally, the evaluation unit 92 derives a ratio Cr1/Cr0 or Cr0/Cr1 between the compression ratio Cr1 and the compression ratio Cr0 as the antifog property evaluation index.

In this example, since the object image has high contrast as mentioned above, the object image 200 is similar to a substantially binary image. Thus, the compression ratio Cr0 has a high value. In the object image 201, on the other hand, as the degree of light scattering due to the fogging of the sample 100 increases, the degree of change in the level of gray, i.e., the pixel value P increases. Thus, the compression ratio Cr1 has a lower value accordingly. When there is almost no light scattering due to fogging, the compression ratio Cr1 has a value close to the compression ratio Cr0.

Therefore, when the ratio Cr1/Cr0 is derived as the antifog property evaluation index, the antifog property of the sample 100 becomes higher as the value of the antifog property evaluation index becomes larger (closer to 1), and the antifog property of the sample 100 becomes lower as the value of the antifog property evaluation index becomes smaller. When the ratio Cr0/Cr1 is derived as the antifog property evaluation index, the opposite applies.

Note that the antifog property evaluation index may be derived using not the compression ratios Cr0 and Cr1 but the compressed file capacities C0 and C1. Alternatively, the value of the compression ratio Cr1 or the values of the compressed file capacities C0 and C1 may be directly used as the antifog property evaluation index as with the cases of the above-described methods. Moreover, the image format of the uncompressed object images 200o and 201o and the image format of the compressed object images 200 and 201 may adopt various known image formats without being limited to any particular image format. Also, the image compression method is not limited to any particular method. For example, the antifog property evaluation index may be derived on the basis of the compression ratios Cr0 and Cr1 when the object images 200o and 201o are compressed in a ZIP format.

If the object 70 having a complicated configuration as shown in FIGS. 2C and 2D is used, for example, the degree of change in the pixel value P may decrease as the degree of light scattering due to fogging increases. As a result, the compression ratio Cr1 may be lower than the compression ratio Cr0. Therefore, it is preferred in the compression ratio method to check the relationship between the value of the antifog property evaluation index and the antifog property beforehand depending on the object 70 to be used.

<Histogram Method>

Figure 9A:
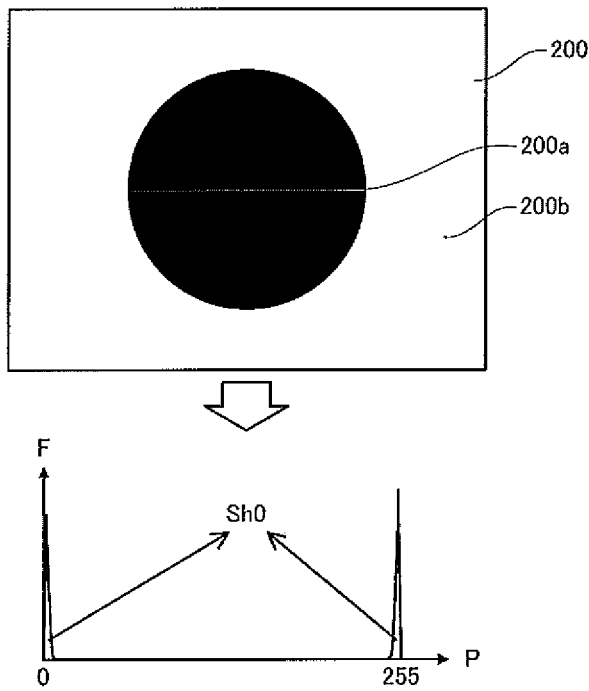
FIGS. 9A and 9B are schematic diagrams showing a general concept of a histogram method.
Figure 9B:
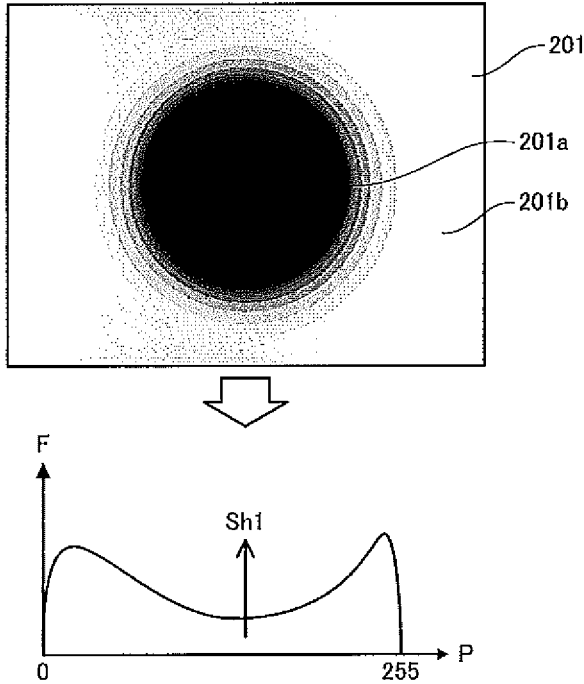

FIGS. 9A and 9B are schematic diagrams showing a general concept of the histogram method. In the histogram method, the antifog property evaluation index is derived based on histogram areas Sh0 and Sh1 of pixel values P in the object images 200 and 201 before and after the generation of fogging. Specifically, the evaluation unit 92 of the control device 90 first generates a histogram, wherein the longitudinal axis thereof represents appearance frequency F and the horizontal axis thereof represents the pixel value P, about the object image 200 acquired when no fogging is present on the sample 100 as shown in FIG. 9A. The evaluation unit 92 then derives the area Sh0 of the generated histogram.

Next, the evaluation unit 92 generates, as with the object image 200, a histogram, wherein the longitudinal axis thereof represents the appearance frequency F and the horizontal axis thereof represents the pixel value P, about the object image 201 acquired when fogging is present on the sample 100 as shown in FIG. 9B. The evaluation unit 92 then derives the area Sh1 of the generated histogram. Thereafter, the evaluation unit 92 derives a ratio Sh1/Sh0 or Sh0/Sh1 between the area Sh1 and the area Sh0 as the antifog property evaluation index.

In this example, since the object image 200 has high contrast as mentioned above, the appearance frequencies F of the pixel values P in the object image 200 are concentrated around values in the vicinity of the minimum value (0) and the maximum value (255), resulting in the small histogram area Sh0. In the object image 201, on the other hand, as the degree of light scattering due to the fogging of the sample 100 increases, the appearance frequencies F of the intermediate pixel values P increase, resulting in the large histogram area Sh1. When there is almost no light scattering due to fogging, on the other hand, the area Sh1 has a value close to the area Sh0.

Therefore, when the ratio Sh1/Sh0 is derived as the antifog property evaluation index, the antifog property of the sample 100 becomes higher as the value of the antifog property evaluation index becomes smaller (closer to 1), and the antifog property of the sample 100 becomes lower as the value of the antifog property evaluation index becomes larger inversely with the above-described methods. When the ratio Sh0/Sh1 is derived as the antifog property evaluation index, the opposite applies.

As with the cases of the above-described methods, the value of the area Sh1 may be directly used as the antifog property evaluation index. When the object images 200 and 201 are acquired as color images, the median value, average value, or weighted average value, for example, of the R value, the G value, and the B value or the H value, the S value, and the V value may be used as the pixel value P. Alternatively, any one of the R value, the G value, and the B value, or any one of the H value, the S value, and the V value may be used as the pixel value P. When the object 70 having a complicated configuration as shown in FIG. 2D is used, in particular, a more appropriate antifog property evaluation index may be derived by limiting the histogram to any one of the R value, the G value, and the B value, or any one of the H value, the S value, and the V value.

The evaluation unit 92 of the control device 90 derives the antifog property evaluation index using any one of the above-described methods. A user may select which one of these methods to use by hand, or the evaluation unit 92 may determine which one of the methods to use in accordance with, for example, the type of the object 70 or the configuration of the acquired object image 200.

As described above, the antifog property evaluating apparatus 1 according to the present embodiment includes: the fogging generation device (the sample stage 10 and the steam spray device 30) configured to generate the fogging of the surface 101 of the sample 100; the object 70 disposed at a position different from that of the sample 100; the imaging device 40 configured to image the object 70 via the sample 100; and the evaluation device (the evaluation unit 92 of the control device 90) configured to evaluate the antifog property of the sample 100 on the basis of the object images 200 and 201 acquired by imaging the object 70.

Such a configuration allows for the imaging of the object 70 via the sample 100 under circumstances similar to the actual use conditions of the sample 100 such as when an outside view is seen through a car window or when a face reflected on a mirror is seen, for example, and allows for evaluation on the antifog property of the sample 100 on the basis of the resultant object images 200 and 201. Thus, the antifog property can be evaluated quantitatively and objectively in a more realistic situation.

The antifog property evaluating apparatus 1 also includes the image-adjusting lens optical system 81 disposed between the sample 100 and the object 70. This allows an image of the object 70 with an appropriate size to be imaged in a more natural state.

The antifog property evaluating apparatus 1 also includes the lighting device 60 configured to illuminate the object 70 from behind. This allows for the acquisition of the high-contrast object images 200 and 201, and thus the evaluation of the antifog property based on the object images 200 and 201 can be performed with high accuracy.

The antifog property evaluating apparatus 1 also includes the surface imaging lens optical system 82 to be disposed between the sample 100 and the imaging device 40 and the retracting device 83 configured to retract the surface imaging lens optical system 82 from the optical path. This allows for the imaging of the state of the surface 101 of the sample 100 by the imaging device 40. Thus, the antifog property can be evaluated in a more multilateral way.

The evaluation device (the evaluation unit 92 of the control device 90) derives the anti fog property evaluation index of the sample 100 on the basis of change in the object image 201 acquired when fogging is generated on the surface of the sample 100 by the fogging generation device (the sample stage 10 and the steam spray device 30). This allows for the evaluation of the antifog property based on the degree of change in the visibility of sight via the sample 100. Thus, the antifog property can be directly evaluated in a more realistic situation.

The evaluation device (the evaluation unit 92 of the control device 90) derives the antifog property evaluation index on the basis of the areas S0 and S1 of the regions A0 and A1 where the pixel values P are smaller than or equal to, or larger than or equal to, the predetermined threshold Pta in the object images 200 and 201. Thus, the quantitative and objective evaluation of the antifog property based on the antifog property evaluation index can be performed in a simple and highly accurate manner.

The evaluation device (the evaluation unit 92 of the control device 90) derives the antifog property evaluation index on the basis of the rates of change (the average slope angles θ0 and θ1) in the pixel values P on the route R set in the object images 200 and 201. The quantitative and objective evaluation of the antifog property based on the antifog property evaluation index can be performed in a simple and highly accurate manner also in this case.

The evaluation device (the evaluation unit 92 of the control device 90) derives the antifog property evaluation index on basis of the differences ΔP0 and ΔP1 or ratios between the pixel values P at the first comparison point La and the second comparison point Lb set in the object images 200 and 201. The quantitative and objective evaluation of the antifog property based on the antifog property evaluation index can be performed in a simple and highly accurate manner also in this case.

The evaluation device (the evaluation unit 92 of the control device 90) derives the antifog property evaluation index on the basis of the distances D0 and D1 from the starting point Ls to the goal points Lg0 and Lg1 at which the pixel value P becomes larger than or equal to the predetermined threshold Ptd for the first time on the route R set in the object images 200 and 201. The quantitative and objective evaluation of the antifog property based on the antifog property evaluation index can be performed in a simple and highly accurate manner also in this case.

The evaluation device (the evaluation unit 92 of the control device 90) derives the antifog property evaluation index on the basis of the compression ratios Cr0 and Cr1 when the uncompressed object images 200o and 201o are compressed by a predetermined image compression method or the compressed file capacities C0 and C1. The quantitative and objective evaluation of the antifog property based on the antifog property evaluation index can be performed in a simple and highly accurate manner also in this case.

The evaluation device (the evaluation unit 92 of the control device 90) derives the antifog property evaluation index on the basis of the histogram areas Sh0 and Sh1 of the pixel values P in the object images 200 and 201. The quantitative and objective evaluation of the antifog property based on the antifog property evaluation index can be performed in a simple and highly accurate manner also in this case.

The antifog property evaluating method according to the present embodiment includes: the fogging generation step of generating the fogging of the surface of the sample 100; the imaging step of imaging the object 70 disposed at the position different from that of the sample 100 via the sample 100; and the evaluation step of evaluating the antifog property of the sample 100 on the basis of the object images 200 and 201 acquired by imaging the object 70.

Such a configuration allows for the imaging of the object 70 via the sample 100 under circumstances similar to the actual use conditions of the sample 100 and allows for evaluation on the antifog property of the sample 100 based on the resultant object images 200 and 201. Thus, the antifog property can be evaluated quantitatively and objectively in a more realistic situation.

In the evaluation step, the antifog property evaluation index of the sample 100 is derived on the basis of change in the object images 200 and 201 when fogging is generated on the surface of the sample 100 in the fogging generation step. This allows for the evaluation of the antifog property based on the degree of change in the visibility of sight via the sample 100. Thus, the antifog property can be directly evaluated in a more realistic situation.

While the embodiments of the present invention have been described above, it is to be understood that the antifog property evaluating apparatus and the antifog property evaluating method according to the present invention are not limited to the above-described embodiments and various modifications thereof may be made without departing from the scope of the present invention. Moreover, the functions and effects described in the aforementioned embodiments are merely the recitation of the most preferred functions and effects that can be obtained by the present invention. Functions and effects of the present invention are not limited thereto.

The antifog property evaluating apparatus and the antifog property evaluating method according to the present invention can be utilized for evaluation on the antifog properties of various materials that transmit or reflect light or evaluation on the antifog properties of coating agents to be applied onto the surfaces of various materials.

The entire disclosure of Japanese Patent Application No. 2015-216697 filed Nov. 4, 2015 including specification, claims, drawings, and summary are incorporated herein by reference in its entirety.

What is claimed is:

1. An antifog property evaluating apparatus comprising:
a fogging generation device configured to generate fogging of a surface of a sample;
an object disposed at a position different from that of the sample;
an imaging device configured to image the object via the sample;
an evaluation device configured to evaluate an antifog property of the sample on a basis of an object image acquired by imaging the object; and
an image-adjusting lens optical system disposed between the sample and the object.

2. The antifog property evaluating apparatus according to claim 1, comprising a lighting device configured to illuminate the object with light from behind.

3. An antifog property evaluating apparatus comprising:
a fogging generation device configured to generate fogging of a surface of a sample;
an object disposed at a position different from that of the sample;
an imaging device configured to image the object via the sample;
an evaluation device configured to evaluate an antifog property of the sample on a basis of an object image acquired by imaging the object;
a surface imaging lens optical system to be disposed between the sample and the imaging device; and
a retracting device configured to retract the surface imaging lens optical system from an optical path.

4. The antifog property evaluating apparatus according to claim 1, comprising:
a surface imaging lens optical system to be disposed between the sample and the imaging device; and
a retracting device configured to retract the surface imaging lens optical system from an optical path.

5. An antifog property evaluating apparatus comprising:
a fogging generation device configured to generate fogging of a surface of a sample;
an object disposed at a position different from that of the sample;
an imaging device configured to image the object via the sample;
an evaluation device configured to evaluate an antifog property of the sample on a basis of an object image acquired by imaging the object;
a measuring chamber configured to house the sample; and
an observation window provided within the measuring chamber, wherein the object is disposed outside the measuring chamber, and wherein an image of the object passes through the observation window and travels toward the surface of the sample; and
wherein the imaging device images the object reflected on the surface of the sample.

6. The antifog property evaluating apparatus according to claim 1, wherein the evaluation device derives an antifog property evaluation index of the sample on a basis of change in the object image when fogging is generated on the surface of the sample by the fogging generation device.

7. An antifog property evaluating apparatus comprising:
a fogging generation device configured to generate fogging of a surface of a sample;
an object disposed at a position different from that of the sample;
an imaging device configured to image the object via the sample; and
an evaluation device configured to evaluate an antifog property evaluation index of the sample on a basis of an object image acquired by imaging the object, wherein the evaluation device derives the antifog property evaluation index of the sample on a basis of change in the object image when fogging is generated on the surface of the sample by the fogging generation device, and wherein the evaluation device derives the antifog property evaluation index on a basis of an area of a region where a pixel value is smaller than or equal to, or larger than or equal to, a predetermined threshold in the object image.

8. An antifog property evaluating apparatus comprising:
a fogging generation device configured to generate fogging of a surface of a sample;
an object disposed at a position different from that of the sample;
an imaging device configured to image the object via the sample; and
an evaluation device configured to evaluate an antifog property evaluation index of the sample on a basis of an object image acquired by imaging the object, wherein the evaluation device derives the antifog property evaluation index of the sample on a basis of change in the object image when fogging is generated on the surface of the sample by the fogging generation device, and wherein the evaluation device derives the antifog property evaluation index on a basis of a rate of change in pixel values on a route set in the object image.

9. An antifog property evaluating apparatus comprising:
a fogging generation device configured to generate fogging of a surface of a sample;
an object disposed at a position different from that of the sample;

an imaging device configured to image the object via the sample; and an evaluation device configured to evaluate an antifog property evaluation index of the sample on a basis of an object image acquired by imaging the object, wherein the evaluation device derives the antifog property evaluation index of the sample on a basis of change in the object image when fogging is generated on the surface of the sample by the fogging generation device, and wherein the evaluation device derives the antifog property evaluation index on a basis of a difference or a ratio between pixel values at a first comparison point and a second comparison point in the object image.

10. The antifog property evaluating apparatus according to claim 9, wherein the first comparison point is in a dark region, and the second comparison point is in a light region; and the evaluation device derives the antifog property evaluation index on a basis of an increase of pixel values at the first comparison point and a decrease of the second comparison point.

11. An antifog property evaluating apparatus comprising:

a fogging generation device configured to generate fogging of a surface of a sample;

an object disposed at a position different from that of the sample;

an imaging device configured to image the object via the sample;

an evaluation device configured to evaluate an antifog property evaluation index of the sample on a basis of an object image acquired by imaging the object, wherein the evaluation device derives the antifog property evaluation index of the sample on a basis of change in the object image when fogging is generated on the surface of the sample by the fogging generation device, and wherein the evaluation device derives the antifog property evaluation index on a basis of a distance from a starting point to a goal point at which a pixel value first becomes larger than or equal to a predetermined threshold on a route set in the object image.

12. An antifog property evaluating apparatus comprising:

a fogging generation device configured to generate fogging of a surface of a sample;

an object disposed at a position different from that of the sample;

an imaging device configured to image the object via the sample; and an evaluation device configured to evaluate an antifog property evaluation index of the sample on a basis of an object image acquired by imaging the object, wherein the evaluation device derives the antifog property evaluation index of the sample on a basis of change in the object image when fogging is generated on the surface of the sample by the fogging generation device, and wherein the evaluation device derives the antifog property evaluation index on a basis of a compression ratio when the object image in an uncompressed state is compressed by a predetermined compression method or a file capacity after compression.

13. An antifog property evaluating apparatus comprising:

a fogging generation device configured to generate fogging of a surface of a sample;

an object disposed at a position different from that of the sample;

an imaging device configured to image the object via the sample; and an evaluation device configured to evaluate an antifog property evaluation index of the sample on a basis of an object image acquired by imaging the object, wherein the evaluation device derives the antifog property evaluation index of the sample on a basis of change in the object image when fogging is generated on the surface of the sample by the fogging generation device, and wherein the evaluation device derives the antifog property evaluation index on a basis of a histogram area of pixel values in the object image.

* * * * *